United States Patent [19]
Riedel et al.

[11] Patent Number: 6,124,585
[45] Date of Patent: Sep. 26, 2000

[54] APPARATUS FOR MEASURING THE REFLECTANCE OF STRIPS HAVING NON-UNIFORM COLOR

[75] Inventors: Richard A. Riedel, Carmel; James S. Hutchison, Indianapolis, both of Ind.

[73] Assignee: UMM Electronics, Inc., Indianapolis, Ind.

[21] Appl. No.: 09/179,500

[22] Filed: Oct. 27, 1998

[51] Int. Cl.$^7$ .................................................. G01N 21/47

[52] U.S. Cl. ................................ 250/208.1; 250/339.11; 356/445

[58] Field of Search ................................ 250/205, 208.1, 250/208.2, 339.11, 559.4; 356/444, 445, 446

[56] References Cited

U.S. PATENT DOCUMENTS

| | | |
|---|---|---|
| 3,244,062 | 4/1966 | Sweet ........................................ 356/445 |
| 3,792,235 | 2/1974 | Durante et al. . |
| 4,113,343 | 9/1978 | Pole et al. . |
| 4,560,862 | 12/1985 | Eastman et al. . |
| 4,978,860 | 12/1990 | Bayley et al. . |
| 5,010,241 | 4/1991 | Butterworth . |
| 5,110,212 | 5/1992 | Gabura ....................................... 356/446 |
| 5,136,150 | 8/1992 | Fukushima et al. . |
| 5,146,082 | 9/1992 | Abe . |
| 5,349,180 | 9/1994 | Vaughan . |
| 5,522,389 | 6/1996 | Fischer et al. . |
| 5,541,413 | 7/1996 | Pearson et al. ....................... 250/339.11 |
| 5,646,683 | 7/1997 | Motta . |
| 5,995,236 | 11/1999 | Roth et al. ................................ 356/445 |

*Primary Examiner*—Stephone B. Allen
*Attorney, Agent, or Firm*—Woodard, Emhardt, Naughton, Moriarty & McNett

[57] ABSTRACT

An optical system for measuring the reflectance of flat strips having potentially optically non-uniform surfaces. In one embodiment the systems includes an array of discrete light sources, wherein each light source is driven by its own individual current, such that the pattern reflected onto a photodector is substantially uniform in intensity.

19 Claims, 5 Drawing Sheets

APPARATUS FOR MEASURING THE REFLECTANCE OF STRIPS HAVING NON-UNIFORM COLOR

TECHNICAL FIELD OF THE INVENTION

The present invention relates generally to the field of optics, and more specifically to the detection of reflectance from a sample along a linear region.

BACKGROUND OF THE INVENTION

The calorimetric measurement of reagent strips or films is an important analytical tool in the fields of clinical chemistry and analytical medicine. Colorimetric optical measurements are often used to measure the concentration of chemical analytes. The known colorimetric optical analysis systems usually includes a continuous light source, a sample, and an optical detector aligned such that the light from the light source shines with approximately even intensity onto the sample and is then reflected as evenly as possible onto the detector. In a typical known colorimetric optical analysis system, the continuous light source is an incandescent bulb or a fluorescent tube. The known colorimetric measurement systems thus have mobility limited by the bulk, weight, and geometry of their components.

Optical analyses involving the measurement of light reflected from a flat diffusing surface are subject to Lambert's Law. Lambert's Law states that the luminous intensity in a given direction radiated or reflected by a perfectly diffusing plane surface varies as the cosine of the angle between that direction and the normal to the surface ($\cos\Theta'$). (See FIG. 7) The efficiency of any optical detector depends upon its projected area and varies as the cosine of the angle of incidence between the normal to the surface and the incident ray ($\cos\Theta$). Therefore, in situations where the light source shines onto a finite planar surface and where the reflected light is then measured by a detector situated coplanar to the light source, $\Theta=\Theta'$ and the decreased intensity from the edges as a function of $\Theta$ may be expressed as $I(\Theta)=I_o\cos^2\Theta$, where $I_o$ is the intensity of the light source.

The concentration of an analyte on a reagent strip sample may be calculated by measuring the optical reflectance from an area of color development on the strip. Whenever the area of color development is non-uniform, or if it consists of a series of dark narrow lines on a brighter background, an optical system capable of resolving the non-uniformity and/or narrow lines must be used. For systems having non-uniform color development, multiple photodiodes can provide some improvement in error associated with the optical non-uniformity. When the color development consists of narrow lines, a distributed detector or a motor with a lensed photodiode has been used to compensate. In many cases, the size of the developing area may be considerable, especially in the case of lateral flow strips where a series of narrow lines develops over a length of up to 25 mm or more. Because the intensity of the signal reflected from the edges of the sample becomes attenuated, the signal-to-noise ratio of the prior art systems decreases below acceptable levels near the edges of the area of interest. This edge attenuation has been compensated for by aperturing a continuous light source such that more light is incident on the edges of the illuminated region. Because such a system requires a continuous light source, such as a fluorescent tube, it is of limited value when the sample is small.

Furthermore, known optical reflectance measurement systems usually require a motor to move the sample under the optics or to move the optics over the irregularly patterned sample. A motor and its required electronic and mechanical support adds bulk, cost, and complexity to the system.

Some known colorimetric analysis systems use one or more discrete light sources, such as light emitting diodes (LEDs) instead of using a continuous light source. However, known systems using a plurality of LEDs as their light source group them in arrays that approximate the light emitted from a continuous source. Furthermore, LEDs cannot be apertured to increase their effective edge illumination intensities. All of these known calorimetric analysis systems employ Lambertian light sources that illuminate the sample less intensely at the edges. Hence, there is a need for an improved optical analysis device for preferentially illuminating the edges of planar samples without resorting to the addition of a motor. A means for satisfying this need has so far eluded those skilled in the art.

SUMMARY OF THE INVENTION

In one embodiment of the present invention, a series of discrete electric light sources are mounted on a printed circuit board. The light sources are geometrically positioned to generate a non-uniform light pattern on the target surface with the edges being more intensely illuminated than the center. Furthermore, the discrete light sources are each driven by a different, pre-determined current to further define the non-uniform illumination pattern. The non-uniform illumination pattern has intensity gradients calculated to correct the $\cos^2\Theta$ loss associated with a Lambertian illumination source. One object of the present invention is to provide an improved optical illumination system. Related objects and advantages of the present invention will be apparent from the following description.

The present invention relates to a non-Lambertian illumination source mounted on a circuit board and shining on a planar sample. The light from the non-Lambertian source is reflected from the sample to a mirror, directed through a focusing lens, and reflected from a second mirror onto an optical detector. The sample surface is maintained as a finite planar surface coplanar with the detector array, so $\Theta=\Theta'$. In one embodiment, the light sources are seven individual LEDs, arranged in a pre-determined pattern or configuration and each driven by its own predetermined current. The LEDs are mounted on the top surface of a circuit board. The configuration of the LEDs and the driving currents are such that the LEDs together emit an illumination pattern suitable for reflecting from a flat surface located a short distance from the LEDs. An opening in the circuit board allows the reflected light to be directed by a mirror mounted under the circuit board through a pair of focusing lenses. A second mirror directs the focused light onto an optical detector mounted beneath the same circuit board. Mounting the LEDs and the photodetector on the same board and using mirrors to direct the beam eliminates the size, bulk and cost associated with the use of a separate circuit board for each and the associated electrical wiring and mechanical support.

DETAILED DESCRIPTION OF THE PREFERRED EMBODIMENT

Figure 1:
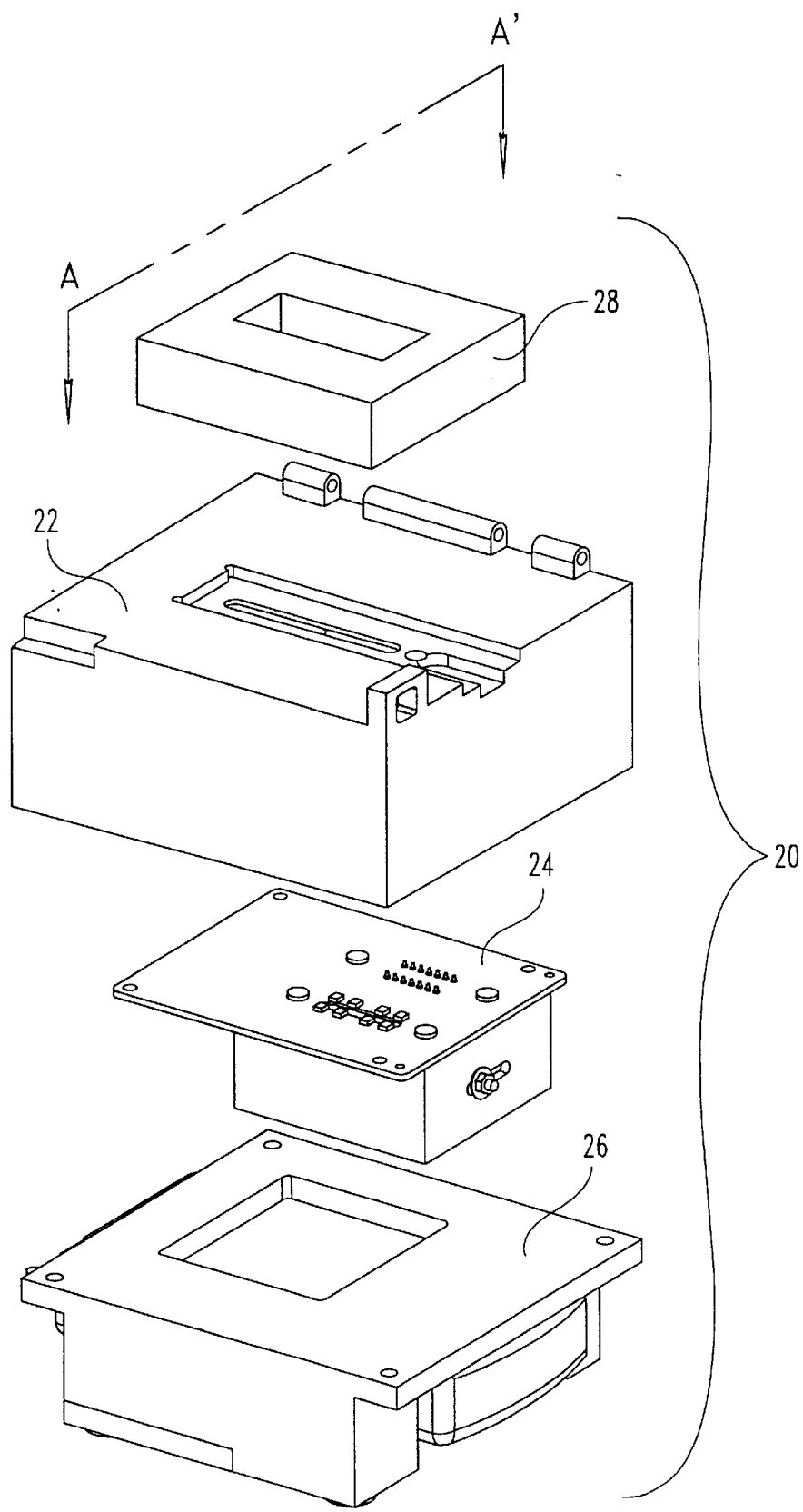
FIG. 1 is an exploded perspective view of a first reflectance gauge of the present invention.
Figure 2:
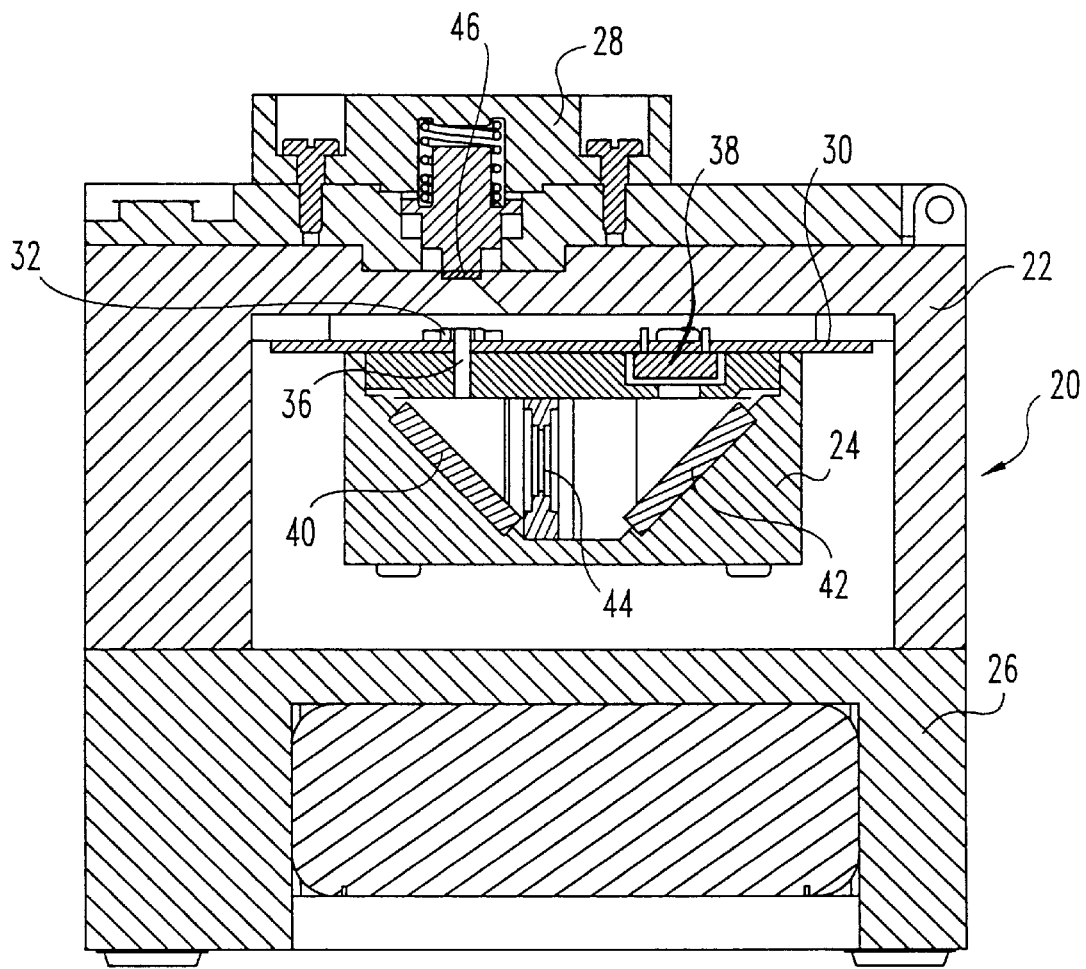
FIG. 2 is a cross-sectional view of the gauge of FIG. 1 taken along line AA'.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIGS. 1–4 illustrate one form of the present invention, an optical reflectance gauge 20 including a housing 22 encompassing a printed circuit board (PCB) assembly 24 and a base assembly 26. A sample holder 28 is mounted to the exterior of housing 22.

PCB assembly 24 includes a circuit board 30 having a plurality of light emitting diodes (LEDs) 32 mounted thereon in a predetermined pattern 34 around a slit 36. The slit 36 is an optical pathway for light to travel through the opaque circuit board 30. The LEDs 32 are mounted on one side of the circuit board 30. An optical detector array 38 is mounted to the reverse side of the same circuit board 30. A first mirror 40 is positioned below the slit 36 at an angle of about 315 degrees to the circuit board 30. A second mirror 42 is positioned beneath the optical detector array 38 at an angle of about 225 degrees to the circuit board 30, such that a substantially 90-degree angle exists between first and second mirrors 40 and 42. A focusing lens 44 is positioned between the first and second mirrors 40, 42. A flat optical sample 46 is mounted in the sample holder 28 above the LED array 34.

In operation, light emitted from the LED array 34 illuminates the sample 46 and is reflected therefrom through the slit 36 to the first mirror 40, from the first mirror 40 through the focusing lens 44 to the second mirror 42, and from the second mirror 42 onto the optical detector array 38. The light striking the optical detector 38 causes the optical detector 38 to generate a measurable voltage.

Figure 4:
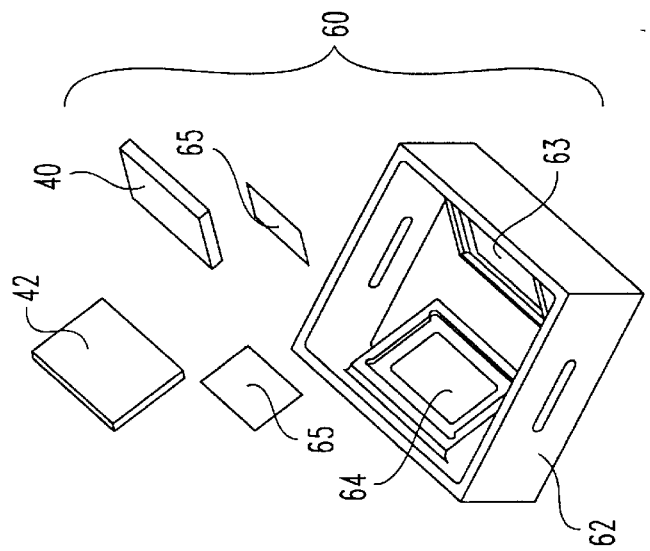
FIG. 4 is an exploded perspective view the mirror assembly housing of FIG. 3.
Figure 3:
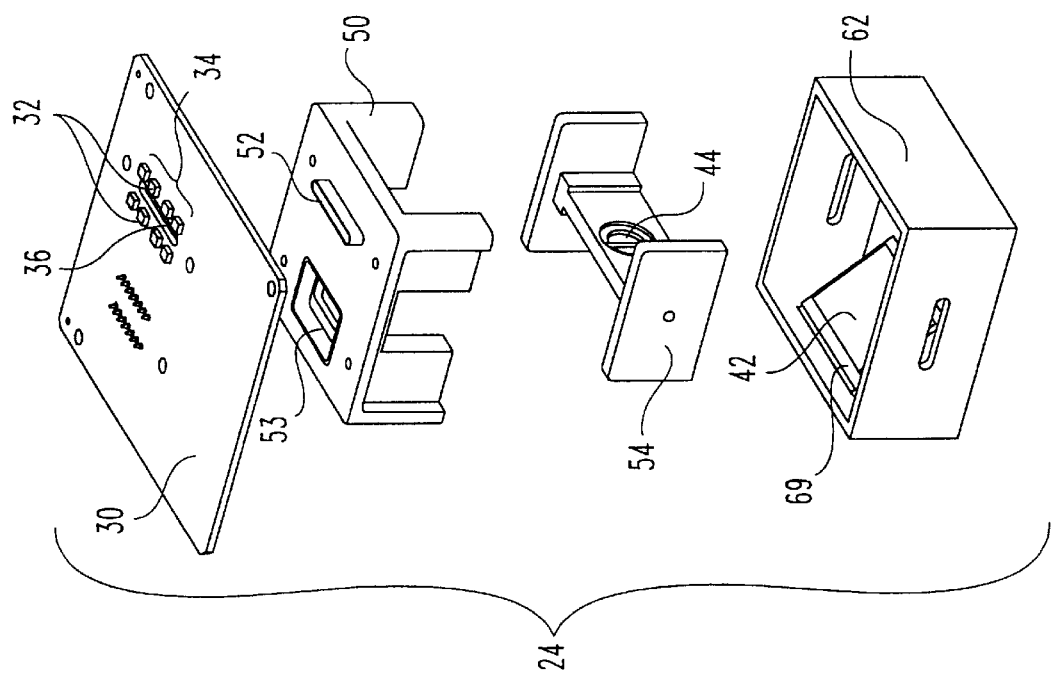
FIG. 3 is an exploded perspective view of the PCB assembly of FIG. 1.

FIGS. 3 and 4 illustrate the PCB assembly 24 of the preferred embodiment in detail. The circuit board 30 is aligned with an optics housing 50. The optics housing 50 also includes an aperture 52 formed therethrough, and the slit 36 in the circuit board 30 is aligned with the aperture 52 in the optics housing 50 to allow light to pass therethrough. The optics housing 50 also includes a recess 53 in which the photodetector 38 may sit. The optics housing 50 rests below the circuit board 30 and above a lens holder 54. The lens holder 54 includes the focusing lens 44 mounted therein. The lens holder 54 rests inside a mirror housing assembly 60, which includes a mirror housing 62 having a pair of angled supports 63, 64 holding the first mirror 40 under he slit 36 and aperture 52 and also holding the second mirror 42 under the optical detector 38, respectively, with the focusing lens 44 situated therebetween. The supports 63, 64 hold the first and second mirrors 40, 42 at a 90-degree angle relative to one another. The mirrors 40, 42 are fastened to their respective supports 63, 64 by fasteners 65. In this embodiment, the fasteners 65 are double-sided tape, although any convenient fastening means may be chosen.

Figure 5:
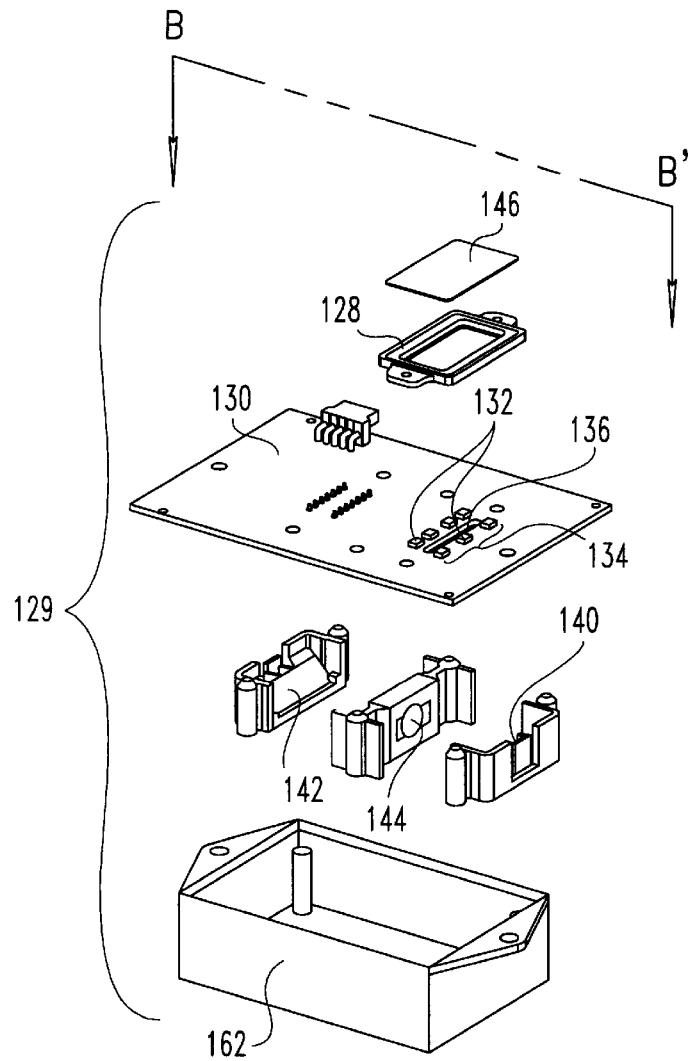
FIG. 5 is an exploded perspective view of the PCB assembly of a second embodiment of the present invention.
Figure 6:
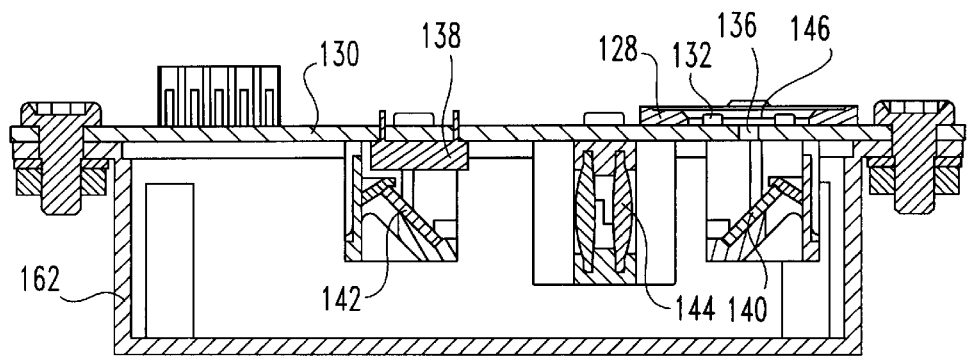
FIG. 6 is a cross-sectional view of the assembly of FIG. 5 taken along line BB'.

Another form of the present invention is shown in FIGS. 5 and 6. FIG. 5 shows a printed circuit board assembly 129 comprising a first mirror 140, a lens 144, and a second mirror 142 mounted directly into a mirror housing 162. A circuit board 130 covers the mirror housing 162, and is oriented such that a slit 136 is positioned directly over the first mirror 140. An array of LEDs 134 is positioned around the slit 136, such that the light emitted therefrom is directed upwardly, away from the slit 136. A sample holder 128 is positioned around the LEDs 134 and is adapted to hold a flat optical sample 146 such that the light from the LEDs 134 illuminates the sample 146 and is reflected back through the slit 136. The first mirror 140 is tilted at a 45 degree angle respective the lens and a 90 degree angle respective the second mirror 142, such that light passing through the slit 136 and incident the first mirror 140 is reflected through the lens 144 to the second mirror 142. Light reflected from the second mirror 142 is directed to a photodetector array 138 affixed to the underside of the circuit board 130 and positioned to receive light reflected from the second mirror 142.

In operation, the LEDs 32 are arranged in a predetermined pattern 34 and are each driven by an individual, predetermined current such that the light emitted from the patterned array 34 corrects for the Lambertian effects varying the illumination of the detector array arising from geometry of the path of the light travelling from the LEDs 32 to the sample 46 and then from the sample to the detector array 38. The sample 46 itself is not necessarily illuminated evenly; however, the reflected image of the sample 46 that reaches the detector array 38 is corrected for the $\cos^2\Theta$ loss associated with a double Lambertian illumination source (the original LED array 34 and the reflecting sample 46) and appears as a substantially evenly illuminated image.

Figure 7:
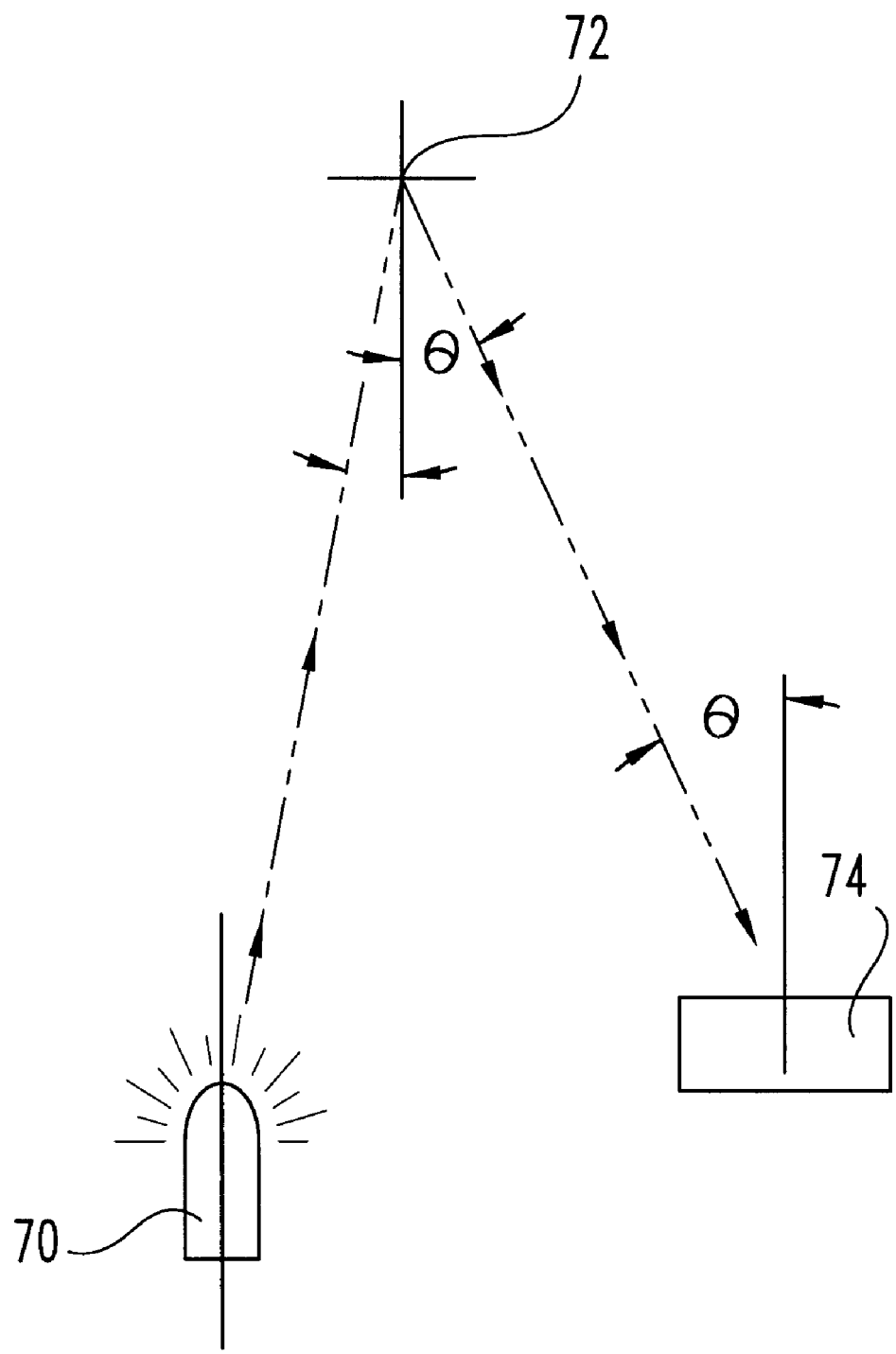
FIG. 7 is an illustrative schematic of the path of a light beam incident on and reflected from a Lambertian surface.

FIG. 7 is an illustrative schematic showing the optical path of a light beam emitted from a light source 70 and reflecting from a Lambertian surface 72 to a detector 74. In the present invention, the light source 70 is an array of discrete, spatially separated electric light emitters, such as, but not limited to, LEDs. Each LED in the array may be illuminated to a predetermined intensity by its own individual current source. The resulting light pattern generated is shone on a flat Lambertian surface 72 positioned at a predetermined distance from the light source 70 and oriented at a predetermined angle $\Theta$ thereto such that the light emission pattern shone on the surface 72 is reflected therefrom through a focussing lens and onto a photodetector array 74. The pattern of the light emitters, the intensity at which each emitter emits light, and the geometry of the emitter array 70, sample, reflectors, and detector array 74 is predetermined such that the intensity of the image striking the detector array 74 is substantially uniform.

In one contemplated embodiment of the present invention, a microprocessor is coupled to the light emitters and to the light detector array. The microprocessor may be used to actuate the light detector array and provide each light source with the appropriate current to generate the desired emission pattern. The microprocessor may also be used to read and store data from the light detector assembly. In one contemplated embodiment, a microprocessor may also be used to adjust the output of the light emitters in the light-emitting array such that the emission pattern striking the light detector array has a uniform intensity. A white optical standard may also be provided for an iterative calibration procedure performed by the microprocessor.

Embodiments of the present invention are contemplated including varied numbers and configurations of light sources, a plurality of focusing lenses, a parabolic mirror instead of a focusing lens, and varied numbers of reflecting mirrors. Other light sources than LEDs are also contemplated, as well as a three-dimensional array of LEDs, to comprise the light-emitting array. Another embodiment of the present invention contemplates mounting the light emitting array and the light detecting array on the same side of a printed circuit board with an opaque light shield therebetween and a mirror assembly adapted to reflect light shone on the sample from the light emitting array to the light detecting array.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A reflectance gauge, comprising:
    a housing;
    a circuit board mounted inside the housing;
    a plurality of discrete illumination sources oriented in a predetermined pattern and mounted on the circuit board;
    a slit formed in the circuit board;
    an optical detector array mounted beneath the circuit board;
    a first mirror coupled to the housing below the slit;
    a focusing lens adapted to receive light from the first mirror;
    a second mirror mounted below the circuit board and positioned to direct light from the focusing lens to the optical detector array.

2. The gauge of claim 1 further comprising flat optical sample holder formed in the housing and adapted to receive light from the plurality of discrete illumination sources.

3. The gauge of claim 1 wherein each of the discrete illumination sources is driven by a separate predetermined current.

4. The gauge of claim 3 further comprising:
    a flat optical sample holder formed in the housing having a flat optical sample held therein;
    wherein a light pattern is generated by the set of discrete illumination sources and wherein the light pattern is adapted to reflect with substantially even intensity onto the optical detector array.

5. The gauge of claim 1 further comprising a microprocessor coupled to the detector array, wherein the microprocessor is adapted to receive and store data from the detector array.

6. The gauge of claim 1 further comprising a data output means coupled to the detector array.

7. The gauge of claim 1 wherein the light sources are LEDs.

8. A reflectance gauge comprising:
    a circuit board having a top side, a bottom side, and a slit formed therethrough;
    a plurality of LEDs mounted in a predetermined pattern to the top side of the circuit board;
    an optical detector array mounted to the bottom side of the circuit board;
    a flat optical sample mounted above the circuit board and positioned to reflect light shining from the LEDs through the slit; and
    a pair of mirrors mounted below the circuit board and positioned to direct light from the slit to the detector;
    wherein each LED is driven by an independent predetermined current and wherein the light shining from the set of LEDs forms an emission pattern.

9. The reflectance gauge of claim 8 wherein the emission pattern is adapted to reflect onto the optical detector array with substantially uniform intensity.

10. The reflectance gauge of claim 8 further comprising a focusing lens positioned between the mirrors.

11. The reflectance gauge of claim 8 wherein the emission pattern is determined by the geometric pattern of the LEDs and the independent current driving each LED.

12. The reflectance gauge of claim 11 wherein the emission pattern is adapted to illuminate the flat optical sample with substantially uniform intensity.

13. The reflectance gauge of claim 8 wherein the emission pattern shining on the flat optical sample has a substantially uniform intensity.

14. The reflectance gauge of claim 8 wherein the emission pattern reflected onto the detector array has a substantially uniform intensity.

15. An optical measurement device, comprising:
    a flat optical sample;
    an LED array having a predetermined pattern adapted to illuminate the flat optical sample; and
    an optical detector array positioned to receive light from the LED array reflected by the flat optical sample;
    wherein each LED is driven by an independent predetermined current and wherein the flat optical sample is illuminated to reflect light with substantially constant intensity onto the optical detector array.

16. The device of claim 15 wherein the LED array and the optical detector array are mounted to opposite sides of the same circuit board.

17. The device of claim 15 further comprising a focusing lens, wherein the light reflected from the flat optical sample is focused through the lens onto the detector array.

18. The device of claim 15 further comprising a mirror, wherein the light reflected by the flat optical sample is directed by the mirror onto the detector array.

19. The device of claim 15 further comprising an optical barrier situated between the LED array and the detector array.

* * * * *